(12) United States Patent
Ivancev

(10) Patent No.: US 9,034,027 B2
(45) Date of Patent: May 19, 2015

(54) PARAPLEGIA PREVENTION STENT GRAFT

(75) Inventor: Krasnodar Ivancev, London (GB)

(73) Assignee: Cook Medical Technologies LLC, Bloomington, IN (US)

( * ) Notice: Subject to any disclaimer, the term of this patent is extended or adjusted under 35 U.S.C. 154(b) by 622 days.

(21) Appl. No.: 13/502,001

(22) PCT Filed: Oct. 13, 2010

(86) PCT No.: PCT/US2010/052446
§ 371 (c)(1),
(2), (4) Date: May 16, 2012

(87) PCT Pub. No.: WO2011/047004
PCT Pub. Date: Apr. 21, 2011

(65) Prior Publication Data
US 2012/0323303 A1 Dec. 20, 2012

Related U.S. Application Data

(60) Provisional application No. 61/278,814, filed on Oct. 13, 2009.

(51) Int. Cl.
*A61F 2/07* (2013.01)
*A61B 19/00* (2006.01)
(Continued)

(52) U.S. Cl.
CPC . *A61F 2/07* (2013.01); *A61B 19/54* (2013.01); *A61F 2002/061* (2013.01); *A61F 2/89* (2013.01); *A61F 2002/075* (2013.01)

(58) Field of Classification Search
USPC ................. 623/1.1–1.16, 1.23, 1.35
See application file for complete search history.

(56) References Cited

U.S. PATENT DOCUMENTS

| | | |
|---|---|---|
| 5,387,235 A | 2/1995 | Chuter |
| 5,425,765 A | 6/1995 | Tiefenbrun et al. |

(Continued)

FOREIGN PATENT DOCUMENTS

| | | |
|---|---|---|
| WO | WO 99/11198 A1 | 3/1999 |
| WO | WO 00/25847 | 5/2000 |

(Continued)

OTHER PUBLICATIONS

International Search Report and Written Opinion of the International Searching Authority, or the Declaration, for PCT/US2010/052446, mailed Jan. 17, 2011 (13p).

(Continued)

*Primary Examiner* — Ryan Severson
(74) *Attorney, Agent, or Firm* — Brinks Gilson & Lione

(57) ABSTRACT

A stent graft (10) for deployment into the aorta of a patient has a tubular body (12) with a proximal portion (14) of a selected diameter and a portion (16) of a reduced diameter less than the selected diameter distal of the proximal portion and a tapered portion (18) extending between the proximal portion and the portion of reduced diameter. Low profile side arms (26, 28, 30, 32) are provided in the portion of reduced diameter and/or the tapered portion. The side arms are for connection of an arm extension to an aortic branch vessel. A paraplegia prevention vent tube (34) is provided in fluid communication with the main lumen and open to external of the tubular body in the region defined by the portion of reduced diameter and the tapered portion. The paraplegia prevention vent tube is not intended to be connected to a side branch of the aorta but is intended, and is so constructed and arranged, to provide temporary perfusion to external of the stent graft after deployment of the stent graft into the aorta and is intended, and is so constructed and arranged, to be subsequently blocked.

16 Claims, 2 Drawing Sheets

(51) Int. Cl.
*A61F 2/06* (2013.01)
*A61F 2/89* (2013.01)

(56) References Cited

U.S. PATENT DOCUMENTS

| | | | |
|---|---|---|---|
| 5,445,600 A | 8/1995 | Abdulla | |
| 5,609,627 A | 3/1997 | Goicoechea et al. | |
| 5,628,783 A | 5/1997 | Quiachon et al. | |
| 5,676,696 A | 10/1997 | Marcade | |
| 5,676,697 A | 10/1997 | McDonald | |
| 5,720,776 A | 2/1998 | Chuter et al. | |
| 5,746,766 A | 5/1998 | Edoga | |
| 5,776,142 A | 7/1998 | Gunderson | |
| 5,824,055 A | 10/1998 | Spiridigliozzi et al. | |
| 5,948,017 A | 9/1999 | Taheri | |
| 5,984,955 A | 11/1999 | Wisselink | |
| 6,019,788 A | 2/2000 | Butters et al. | |
| 6,099,548 A | 8/2000 | Taheri | |
| 6,106,549 A | 8/2000 | Taheri | |
| 6,187,033 B1 | 2/2001 | Schmitt et al. | |
| 6,206,931 B1 | 3/2001 | Cook et al. | |
| 6,210,429 B1 | 4/2001 | Vardi et al. | |
| 6,287,315 B1 | 9/2001 | Wijeratne et al. | |
| 6,478,817 B2 | 11/2002 | Schmitt et al. | 623/1.31 |
| 6,524,335 B1 | 2/2003 | Hartley et al. | |
| 6,576,009 B2 | 6/2003 | Ryan et al. | |
| 6,645,242 B1 | 11/2003 | Quinn | |
| 6,663,666 B1 | 12/2003 | Quiachon et al. | |
| 6,695,875 B2 | 2/2004 | Stelter et al. | |
| 6,723,116 B2 | 4/2004 | Taheri | |
| 6,793,672 B2 | 9/2004 | Khosravi et al. | |
| 6,827,726 B2 | 12/2004 | Parodi | |
| 6,849,087 B1 | 2/2005 | Chuter | |
| 6,918,925 B2 | 7/2005 | Tehrani | |
| 6,939,370 B2 | 9/2005 | Hartley et al. | |
| 6,974,471 B2 | 12/2005 | Van Schie et al. | |
| 7,014,653 B2 | 3/2006 | Ouriel et al. | |
| 7,144,421 B2 | 12/2006 | Carpenter et al. | 623/1.11 |
| 7,169,176 B2 | 1/2007 | Lauterjung | |
| 7,232,459 B2 | 6/2007 | Greenberg et al. | |
| 7,238,198 B2 | 7/2007 | Hartley et al. | |
| 7,294,147 B2 | 11/2007 | Hartley | |
| 7,306,623 B2 | 12/2007 | Watson | |
| 7,407,509 B2 | 8/2008 | Greenberg et al. | |
| 7,435,253 B1 | 10/2008 | Hartley et al. | |
| 7,537,606 B2 | 5/2009 | Hartley et al. | |
| 7,645,298 B2 | 1/2010 | Hartley et al. | |
| 7,699,883 B2 | 4/2010 | Douglas | 623/1.12 |
| 7,771,462 B1 | 8/2010 | Davidson et al. | |
| 7,806,917 B2 | 10/2010 | Xiao | |
| 7,828,837 B2 | 11/2010 | Khoury | 623/1.13 |
| 7,914,572 B2 | 3/2011 | Hartley et al. | 623/1.13 |
| 7,927,367 B2 | 4/2011 | Chuter | |
| 2001/0012943 A1 | 8/2001 | Shaolian et al. | |
| 2001/0012962 A1 | 8/2001 | Schmitt et al. | 623/1.31 |
| 2001/0049534 A1 | 12/2001 | Lachat | |
| 2002/0045930 A1 | 4/2002 | Burg et al. | |
| 2003/0088305 A1 | 5/2003 | Van Schie et al. | |
| 2003/0120332 A1 | 6/2003 | Hartley | |
| 2003/0199967 A1 | 10/2003 | Hartley et al. | |
| 2003/0233140 A1 | 12/2003 | Hartley et al. | |
| 2004/0073289 A1 | 4/2004 | Hartley | |
| 2004/0098079 A1 | 5/2004 | Hartley et al. | |
| 2004/0106972 A1 | 6/2004 | Deaton | |
| 2004/0106978 A1 | 6/2004 | Greenberg et al. | |
| 2004/0215327 A1 | 10/2004 | Doig et al. | |
| 2005/0102018 A1 | 5/2005 | Carpenter et al. | 623/1.11 |
| 2005/0102021 A1 | 5/2005 | Osborne | |
| 2005/0131518 A1 | 6/2005 | Hartley et al. | |
| 2005/0149166 A1 | 7/2005 | Schaeffer et al. | |
| 2005/0171597 A1 | 8/2005 | Boatman et al. | |
| 2005/0171598 A1 | 8/2005 | Schaeffer | |
| 2005/0182476 A1 | 8/2005 | Hartley et al. | |
| 2005/0222668 A1 | 10/2005 | Schaeffer et al. | |
| 2005/0222669 A1 | 10/2005 | Purdy | |
| 2005/0222672 A1 | 10/2005 | Shmulewitz | |
| 2005/0273155 A1 | 12/2005 | Bahler et al. | |
| 2006/0058864 A1 | 3/2006 | Schaeffer et al. | |
| 2006/0089704 A1 | 4/2006 | Douglas | 623/1.12 |
| 2006/0184228 A1 | 8/2006 | Khoury | 623/1.13 |
| 2006/0229707 A1 | 10/2006 | Khoury | |
| 2007/0083215 A1 | 4/2007 | Hamer et al. | |
| 2007/0219614 A1 | 9/2007 | Hartley | |
| 2007/0219621 A1 | 9/2007 | Hartley et al. | 623/1.13 |
| 2007/0233220 A1 | 10/2007 | Greenan | |
| 2007/0244547 A1 | 10/2007 | Greenan | |
| 2007/0250154 A1 | 10/2007 | Greenberg et al. | |
| 2007/0299499 A1 | 12/2007 | Hartley et al. | |
| 2009/0030502 A1 | 1/2009 | Sun et al. | |
| 2009/0048663 A1 | 2/2009 | Greenberg | |
| 2009/0125098 A1 | 5/2009 | Chuter | |
| 2009/0171438 A1 | 7/2009 | Chuter et al. | |
| 2010/0023110 A1 | 1/2010 | Schaeffer | |
| 2010/0063576 A1 | 3/2010 | Schaeffer et al. | |
| 2010/0249899 A1 | 9/2010 | Chuter et al. | |
| 2010/0268327 A1 | 10/2010 | Bruszewski et al. | |
| 2011/0054594 A1 | 3/2011 | Mayberry et al. | |
| 2012/0041535 A1 | 2/2012 | Huser et al. | |
| 2012/0323303 A1 | 12/2012 | Ivancev | |
| 2013/0046371 A1 | 2/2013 | Greenberg et al. | |

FOREIGN PATENT DOCUMENTS

| | | |
|---|---|---|
| WO | WO 2004/002365 A1 | 1/2004 |
| WO | WO 2004/002370 A1 | 1/2004 |
| WO | WO 2004/017867 A1 | 3/2004 |
| WO | WO 2004/017868 A1 | 3/2004 |
| WO | WO 2004/028399 A2 | 4/2004 |
| WO | WO 2005/034808 A1 | 4/2005 |
| WO | WO 2005/034810 A1 | 4/2005 |
| WO | WO 2008/007397 A1 | 1/2008 |
| WO | WO 2010/127040 A1 | 11/2010 |
| WO | WO 2011/047004 A1 | 4/2011 |
| WO | WO 2011/116308 A1 | 9/2011 |

OTHER PUBLICATIONS

Extended European Search Report, dated Mar. 5, 2014 for corresponding European Patent Application No. 13275292.4 (5 pages).
Partial European Search Report, dated Dec. 14, 2012, European Patent Application No. 12164809.1, European Patent Office, The Netherlands (6 pages).
Extended European Search Report, dated Apr. 16, 2013 for corresponding European Patent Application No. 12164809.1 (14 pages).

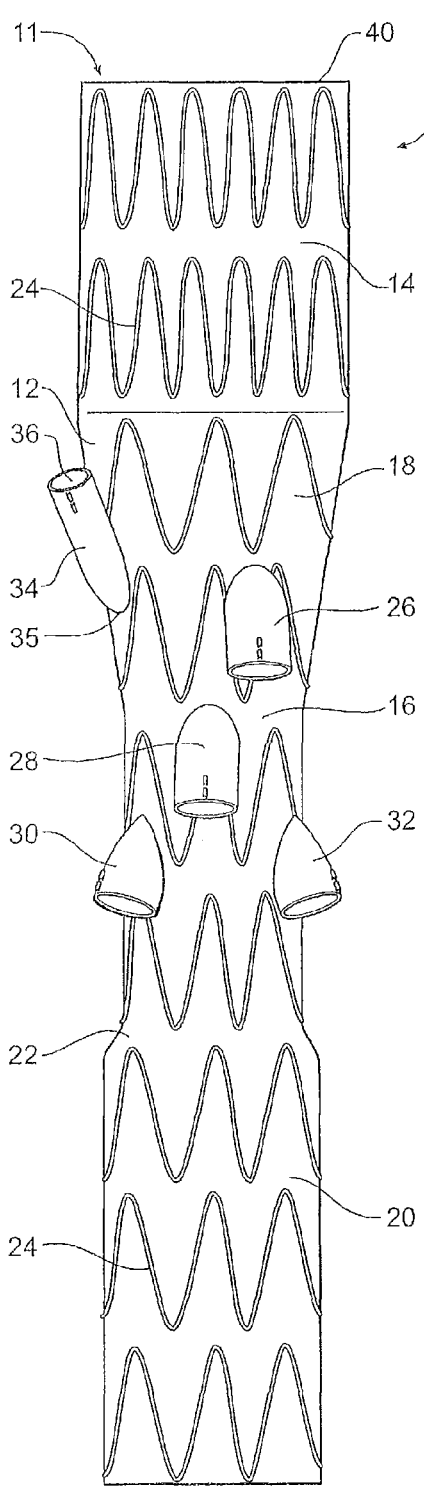
Fig 1
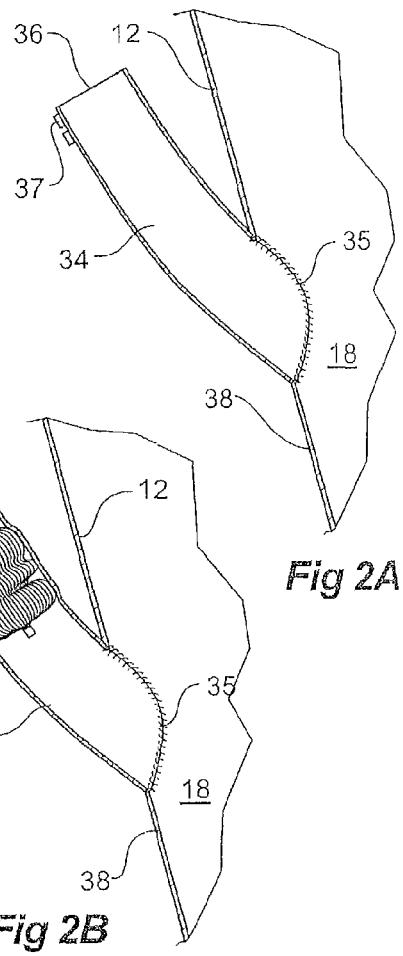
Fig 2A
Fig 2B
Fig 2C

PARAPLEGIA PREVENTION STENT GRAFT

RELATED APPLICATIONS

This is an Application filed under 35 USC 371 from PCT Application PCT/US2010/052446, filed Oct. 13, 2010, which claims priority of U.S. Provisional Application No. 61/278,814, filed Oct. 13, 2009.

TECHNICAL FIELD

This invention relates to a medical device and more particularly to an implantable endovascular device.

BACKGROUND ART

This invention will be discussed in general with respect to aortic aneurysms and the use of an implantable device such as a stent graft to bridge an aneurysm and in particular in the descending aorta but the invention is not so limited and may be used for any region of the human or animal body and any type of implantable device.

A stent graft can be used to bridge an aortic aneurysm but where there are side branch arteries from the aorta it is necessary to have side branches extending from the stent graft to give a blood supply to as many side branch arteries as possible.

There are four main side branch arteries in the descending aorta. These are the celiac artery, the superior mesenteric artery, the right renal artery and the left renal artery. There are also a number of other minor side branch arteries but these are smaller and generally cannot be catheterized to enable placement of a side branch graft. One of these sets of arteries are the intercostal arteries.

After an endovascular operation to place a stent graft into the descending aorta, the human or animal body can in time adapt to lack of blood supply from some arteries which are excluded by the stent graft. For instance blood supply via the intercostal arteries to the spinal cord can be alternatively achieved via other arteries such as for instance the celiac artery, the superior mesenteric artery, lumbar and internal iliac arteries.

There can be a problem, however, of blood supply immediately after an operation, at least in part relating to blood pressure and it is the object of this invention to provide a possible solution or at least provide the physician with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

DISCLOSURE OF THE INVENTION

In one form therefore the invention is said to reside in an implantable device comprising a tubular body of a biocompatible graft material, the tubular body defining a main lumen therethrough, a plurality of low profile side arms in the tubular body, each low profile side arm comprising a respective side arm lumen therethrough and the main lumen being in fluid communication with the respective side arm lumens, the side arms each being intended, and so constructed and arranged, for connection of an arm extension to a branch vessel, a paraplegia prevention vent tube in fluid communication with the main lumen and open externally in a proximal direction to external of the tubular body, wherein the paraplegia prevention vent tube is not intended to be connected to a side branch vessel; but wherein the paraplegia prevention vent tube is intended, and is so constructed and arranged, to provide perfusion to external of the implantable device after deployment of the implantable device into a vessel of the human or animal body; and wherein the paraplegia prevention vent tube is intended, and is so constructed and arranged, to be subsequently blocked.

In a preferred embodiment the implantable device is intended for deployment into the descending aorta and the plurality of low profile side arms comprises four low profile side arms which are constructed and arranged for connection to the celiac artery, superior mesenteric artery, the right renal artery and the left renal artery; and the paraplegia prevention vent tube is intended for, and is constructed and arranged for, temporary perfusion of the intercostal arteries.

In an alternative form the invention comprises a stent graft for deployment into the aorta of a patient, the stent graft comprising a tubular body of a biocompatible graft material, the tubular body defining a main lumen therethrough, the tubular body comprising a proximal portion of a selected diameter and a portion of reduced diameter which is less than the selected diameter distal of the proximal portion and a tapered portion extending between the proximal portion and the portion of reduced diameter, a plurality of low profile side arms in the portion of reduced diameter or the tapered portion, each low profile side arm comprising a respective side arm lumen therethrough and the main lumen being in fluid communication with the respective side arm lumens, the side arms each being intended for, and so constructed and arranged for connection of an arm extension to an aortic branch vessel, a paraplegia prevention vent tube in fluid communication with the main lumen and open externally in a proximal direction to external of the tubular body in the region defined by the portion of reduced diameter or the tapered portion, wherein the paraplegia prevention vent tube is not intended to be connected to a side branch of the aorta but is intended, and is so constructed and arranged, to provide temporary perfusion externally in a proximal direction to external of the stent graft after deployment of the stent graft into the aorta; and is intended, and is so constructed and arranged, to be subsequently blocked.

Preferably the paraplegia prevention vent tube has an open external end in a proximal direction from where it is mounted to the stent graft which gives an open internal end opening distally to allow for subsequent endoluminal access for instance from an femoral access point for the subsequent blocking.

The paraplegia prevention vent tube can be positioned on the tubular body proximally or distally of the plurality of low profile side arms.

Preferably the paraplegia prevention vent tube has a diameter of approximately 6 mm and a length of from 10 to 32 mm.

Preferably the plurality of low profile side arms in the portion of reduced diameter or the tapered portion comprises four low profile side arms which are intended, and are so constructed and arranged, for connection to the celiac artery, superior mesenteric artery, the right renal artery and the left renal artery.

The tubular body can comprise a distal portion with a diameter less than the selected diameter and greater than that of the portion of reduced diameter distal of the proximal portion and a distal tapered portion extending between the distal portion and the portion of reduced diameter.

In one embodiment the proximal portion has a diameter of approximately 34 mm, the distal portion has a diameter of approximately 24 mm and the portion of reduced diameter can have a diameter of approximately 20 mm.

Preferably the paraplegia prevention vent tube comprises radiopaque markers at its proximal and distal ends to assist with later location by radiographic techniques. For instance there may be to markers in line at the proximal end and three markers in line at the distal end.

In an alternative form the invention comprises an implantable device comprising a tubular body of a biocompatible graft material, the tubular body defining a main lumen therethrough and a paraplegia prevention vent tube in fluid communication with the main lumen and open externally in a proximal direction to external of the tubular body, wherein the paraplegia prevention vent tube is not intended to be connected to a side branch vessel, but is intended, and is so constructed and arranged to provide temporary perfusion to external of the implantable device after deployment of the implantable device into a vessel of the human or animal body; and is intended, and is so constructed and arranged, to be subsequently blocked.

Hence it will be seen that by the various forms of the invention there is provided an arrangement by which, at the time of placement of the implantable device such as a stent graft and side branches, an annular space is defined outside the stent graft by there being the portion of reduced diameter of the stent graft and in the region of the intercostal arteries and these are not closed off to blood supply because blood can still exit the stent graft through the paraplegia prevention vent tube into that annular space. In particular the paraplegia prevention vent tube enables temporary perfusion to that portion of the descending aorta which is occluded by placement of the implantable device to enable temporary continued perfusion of any of the intercostal arteries which may extend from the descending aorta in that region.

This is counter intuitive to normal endovascular device placement because one of the aims of endovascular bridging of an aneurysm is to avoid endoleaks into the excluded portion of the aorta.

Immediately after an operation to deploy an endovascular stent graft, blood pressure in a patient can be low and there may be insufficient blood supplied through the side branch stent grafts to the branch arteries. The continued perfusion of the excluded annular space outside the stent graft in the region of the intercostal arteries enables a continued supply of blood to the vertebral region which can prevent paraplegia. Subsequently, perhaps a week later when blood pressure has risen generally in the patient, the vent tube can be closed off by placement of a vascular plug by endovascular techniques. Continued supply of blood to the vertebral region can then be obtained by blood supply from the placed side branches.

BRIEF DESCRIPTION OF THE DRAWINGS

This then generally describes the invention but to assist with understanding reference will now be made to the accompanying drawings.
In the drawings:
FIG. 1 shows a schematic view of a stent graft according to one embodiment of the invention;
FIG. 2A shows a cross sectional view of the paraplegia prevention vent tube of FIG. 1;
FIG. 2B shows a cross sectional view of the paraplegia prevention vent tube of FIG. 1 closed off with a plug;
FIG. 2C shows a cross sectional view of an alternative embodiment of a paraplegia prevention vent tube.

DESCRIPTION OF PREFERRED EMBODIMENTS

Figure 3:
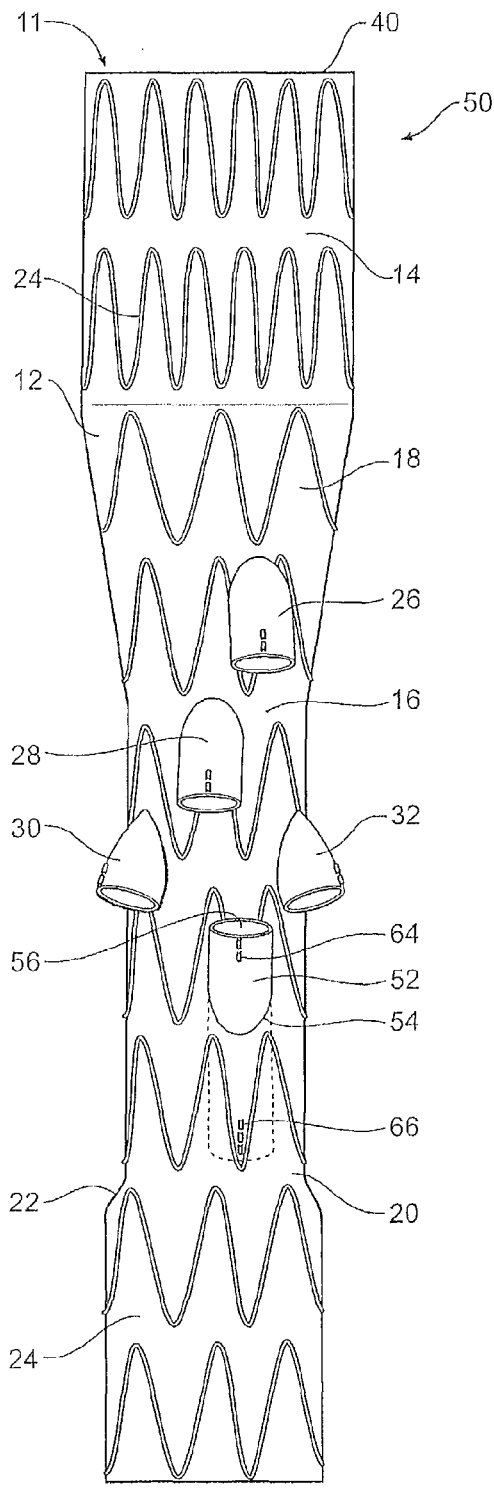
FIG. 3 shows a schematic view of a stent graft according to an alternative embodiment of the invention.

Now looking at the FIGS. 1, 2A and 2B of the drawings in detail, a stent graft 10 according to one embodiment of the invention comprises a tubular body 12 of a biocompatible graft material. The tubular body has a main lumen 11 therethrough. The tubular body comprises a proximal portion 14 of a selected diameter and a portion of reduced diameter 16 less than the selected diameter distal of the proximal portion and a proximal tapered portion 18 extending between the proximal portion 14 and the portion of reduced diameter 16. The tubular body 12 also comprises a distal portion 20 which has a diameter less than the selected diameter and greater than that of the portion of reduced diameter 16 distal of the proximal portion and a distal tapered portion 22 extending between the distal portion 20 and the portion of reduced diameter 16. In this embodiment the proximal portion has a diameter of approximately 34 mm, the distal portion has a diameter of approximately 24 mm and the portion of reduced diameter has a diameter of approximately 20 mm.

Each of the proximal portion, the distal portion and the portion of reduced diameter are supported by stents 24 affixed to the graft material by stitching, adhesive or other method of affixation. The stents may be inside or outside of the tubular body. Each of the stents is preferably a self expanding Gianturco Z-stent formed from Nitinol or stainless steel wire.

There are four low profile side arms 26, 28, 30 and 32 extending from fenestrations in the portion of reduced diameter 16 or the proximal tapered portion 18. Each low profile side arm comprises a respective side arm lumen therethrough and the main lumen is in fluid communication with the respective side arm lumens. Each of the four low profile side arms 26, 28, 30 and 32 are supported by stent structures and can have reinforcing rings at their internal and external ends.

The four low profile side arms 26, 28, 30 and 32 are intended in use to receive extension side arms for entry into the celiac artery, the superior mesenteric artery, the right renal artery and the left renal artery respectively.

US Patent Application Publication Number 20070219621 entitled "Side Branch Stent Graft Construction", now Hartley et al. U.S. Pat. No. 7,914,572, discloses various forms of low profile side arms and the teachings therein are incorporated herein in their entirety.

The tubular body 12 also includes a paraplegia prevention vent tube 34 extending from a fenestration 35 in the proximal tapered portion 18 and in fluid communication with the main lumen 11. The paraplegia prevention vent tube 34 is open to external of the tubular body at 36 in the region defined by the portion of reduced diameter and the tapered portion. The paraplegia prevention vent tube 34 is not intended to be connected to a side branch artery of the aorta but is used to provide temporary perfusion to external of the stent graft after deployment of the stent graft into the aorta and intended to be subsequently blocked.

The paraplegia prevention vent tube 34 can be formed from a biocompatible graft material and have a diameter of 6 mm and a length of from 16 to 32 mm.

FIG. 2A shows a cross sectional view of a paraplegia prevention vent tube 34. The vent tube 34 is connected to the wall 38 of the tubular body 12 at a fenestration 35. The tube 34 is un-stented along its length and has an open proximal end 36.

The paraplegia prevention vent tube 34 has radiopaque markers 37 at its proximal end to assist with later location by radiographic techniques.

FIG. 2B shows a cross sectional view of a paraplegia prevention vent tube closed off with a plug 39. The plug 39 is deployed endovascularly and released into the vent tube 34. The plug may for instance be an Amplatzer Vascular Plug (AGA Medical Corporation, MN, USA). The plug may have suitable over sizing to ensure it seals in the vent tube.

FIG. 2C shows a cross sectional view of an alternative embodiment of a paraplegia prevention vent tube. In this embodiment the vent tube 40 includes a low profile side arm 42 which has a portion 42a external of the wall 38 of the tubular body 12 at a fenestration 35 and a portion 42b internal of the wall 38. Connected to the low profile side arm 42 is a tubular portion 44 with an open proximal end 46. The tubular portion 44 can be stented or unstented along its length.

Figure 4A:
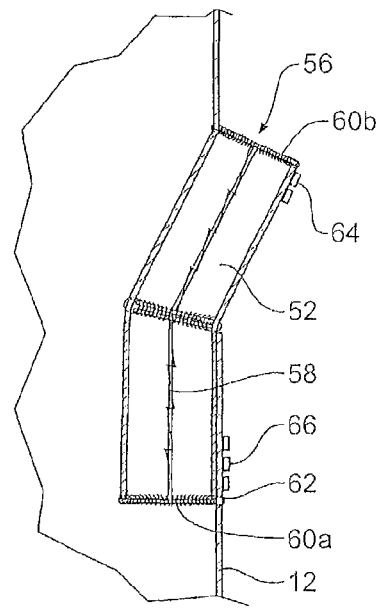
FIG. 4A shows a cross sectional view of the paraplegia prevention vent tube of FIG. 3.
Figure 4B:
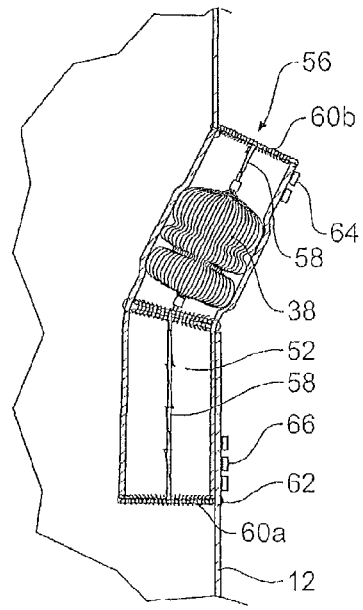
FIG. 4B shows a cross sectional view of the paraplegia prevention vent tube of FIG. 3 closed off with a plug.

Now looking at the FIGS. 3, 4A and 4B drawings corresponding reference numerals are used for items corresponding to those in FIG. 1. The stent graft 50 according to an alternative embodiment of the invention comprises a tubular body 12 of a biocompatible graft material. The tubular body has a main lumen 11 therethrough. The tubular body comprises a proximal portion 14 of a selected diameter and a portion of reduced diameter 16 less than the selected diameter distal of the proximal portion and a proximal tapered portion 18 extending between the proximal portion 14 and the portion of reduced diameter 16. The tubular body 12 also comprises a distal portion 20 which has a diameter less than the selected diameter and greater than that of the portion of reduced diameter 16 distal of the proximal portion and a distal tapered portion 22 extending between the distal portion 20 and the portion of reduced diameter 16. In this embodiment the proximal portion has a diameter of approximately 34 mm, the distal portion has a diameter of approximately 24 mm and the portion of reduced diameter has a diameter of approximately 20 mm.

Each of the proximal portion, the distal portion and the portion of reduced diameter are supported by stents 24 affixed to the graft material by stitching, adhesive or other method of affixation. The stents may be inside or outside of the tubular body. Each of the stents is preferably a self expanding Gianturco Z-stent formed from Nitinol or stainless steel wire.

There are four low profile side arms 26, 28, 30 and 32 extending from fenestrations in the portion of reduced diameter 16 or the proximal tapered portion 18. Each low profile side arm comprises a respective side arm lumen therethrough and the main lumen is in fluid communication with the respective side arm lumens. Each of the four low profile side arms 26, 28, 30 and 32 are supported by stent structures and can have reinforcing rings at their internal and external ends.

The four low profile side arms 26, 28, 30 and 32 are intended in use to receive extension side arms for entry into the celiac artery, the superior mesenteric artery, the right renal artery and the left renal artery respectively.

The tubular body 12 also includes a paraplegia prevention vent tube 52 extending from a fenestration 54 in the portion of reduced diameter 16 and in fluid communication with the main lumen 11. The paraplegia prevention vent tube 52 is open to external of the tubular body at 56 in the region defined by the portion of reduced diameter and the tapered portion. The paraplegia prevention vent tube 52 is not intended to be connected to a side branch artery of the aorta but is used to provide temporary perfusion to external of the stent graft after deployment of the stent graft into the aorta and intended to be subsequently blocked.

The paraplegia prevention vent tube 52 can be formed from a biocompatible graft material and have a diameter of 6 mm and a length of from 16 to 32 mm. The paraplegia prevention vent tube 52 can comprise supporting stents 58 and reinforcing rings 60a and 60b at the internal and external ends respectively.

The paraplegia prevention vent tube comprises radiopaque markers at its proximal and distal ends to assist with later location by radiographic techniques. In this embodiment there are two markers 64 in line at the proximal end and three markers 66 in line on the outside of the tubular body 12 at the distal end of the paraplegia prevention vent.

In a preferred embodiment of the invention the stent graft may have dimensions as follows:

| | |
|---|---|
| Overall length | 236 mm |
| Length of proximal portion | 48 mm |
| Length of tapered portion | 43 mm |
| Length of reduced diameter portion | 71 mm |
| Length of distal portion | 68 mm |
| Diameter of proximal portion | 34 mm |
| Diameter of distal portion | 24 mm |
| Diameter of portion of reduced diameter | 20 mm |

In a preferred embodiment of the invention taking the circumference of the stent graft as a clock face with the anterior point a 12 o'clock the side arms and paraplegia prevention vent tube may be placed as follows:

celiac artery Distance from proximal end 89 mm, 8 mm diameter, length 18 mm, position 1 o'clock superior mesenteric artery Distance from proximal end 110 mm, 8 mm diameter, length 21 mm, position 12 o'clock right renal artery Distance from proximal end 128 mm, 6 mm diameter, length 18 mm, position 10:45 o'clock left renal artery Distance from proximal end 128 mm, 6 mm diameter, length 18 mm, position 2:45 o'clock paraplegia prevention vent tube Distance from proximal end 130 mm, 6 mm diameter, length 32 mm, position 1:30 o'clock FIG. 4A shows a cross sectional view of a paraplegia prevention vent tube 52. The vent tube 52 is connected by stitching 62 to the wall 38 of the tubular body 12.

FIG. 4B shows a cross sectional view of a paraplegia prevention vent tube closed off with a plug 39. The plug 39 is deployed endovascularly and released into the vent tube 52. The plug may for instance be an Amplatzer Vascular Plug (AGA Medical Corporation, MN, USA). The plug may have suitable over sizing to ensure it seals in the vent tube.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft for deployment into the aorta of a patient, the stent graft comprising
a tubular body of a biocompatible graft material, the tubular body defining a main lumen therethrough, the tubular body comprising a proximal portion of a selected diameter, a portion of reduced diameter which is less than the selected diameter distal of the proximal portion, and a tapered portion extending between the proximal portion and the portion of reduced diameter, a plurality of low profile side arms in the portion of reduced diameter or the tapered portion, each low profile side arm comprising a respective side arm lumen therethrough and the main lumen being in fluid communication with the respective side arm lumens, the side arms each being intended, and so constructed and arranged, for connection of an arm extension to an aortic branch vessel, and a paraplegia prevention vent tube in fluid communication with the main lumen and open externally in a proximal direction to external of the tubular body in the region defined by the portion of reduced diameter and the tapered portion, wherein the paraplegia prevention vent tube is not intended to be connected to a side branch of the aorta but wherein the paraplegia prevention vent tube is intended, and is so constructed and arranged, to provide temporary perfusion to external of the stent graft after deployment of the stent graft into the aorta; and wherein the paraplegia prevention vent tube is intended and is so constructed and arranged to be subsequently blocked.

2. A stent graft as in claim 1 wherein the paraplegia prevention vent tube is open internally in a distal direction.

3. A stent graft as in claim 1 wherein the paraplegia prevention vent tube is positioned on the tubular body proximally of the plurality of low profile side arms.

4. A stent graft as in claim 1 wherein the paraplegia prevention vent tube is positioned on the tubular body distally of the plurality of low profile side arms.

5. A stent graft as in claim 1 wherein the paraplegia prevention vent tube has a diameter of approximately 6 mm and a length of from 10 to 32 mm.

6. A stent graft as in claim 1 wherein the plurality of low profile side arms in the portion of reduced diameter or the tapered portions comprises four low profile side arms which are constructed and arranged for connection to the celiac artery, superior mesenteric artery, the right renal artery and the left renal artery.

7. A stent graft as in claim 1 wherein the paraplegia prevention vent tube is unstented.

8. A stent graft as in claim 1 wherein the tubular body comprises a distal portion comprising a diameter less than that of the selected diameter and greater than that of the portion of reduced diameter distal of the proximal portion, and a distal tapered portion extending between the distal portion and the portion of reduced diameter.

9. A stent graft as in claim 8 wherein the proximal portion has a diameter of approximately 34 mm, the distal portion has a diameter of 24 mm and the portion of reduced diameter has a diameter of 20 mm.

10. An implantable device comprising
a tubular body of a biocompatible graft material, the tubular body defining a main lumen therethrough,
a plurality of low profile side arms in the tubular body, each low profile side arm comprising a respective side arm lumen therethrough and the main lumen being in fluid communication with the respective side arm lumens, the side arms each being intended, and so constructed and arranged, for connection of an arm extension to a branch vessel,
a paraplegia prevention vent tube in fluid communication with the main lumen and open externally in a proximal direction to external of the tubular body, wherein the paraplegia prevention vent tube is not intended to be connected to a side branch vessel, but wherein the paraplegia prevention vent tube is intended and is so constructed and arranged to provide temporary perfusion to external of the implantable device after deployment of the implantable device into a vessel of the human or animal body, and wherein the paraplegia prevention vent tube is intended and is so constructed and arranged to be subsequently blocked.

11. An implantable device as in claim 10 wherein the paraplegia prevention vent tube is open internally in a distal direction.

12. An implantable device as in claim 10 wherein the paraplegia prevention vent tube is positioned on the tubular body proximally of the plurality of low profile side arms.

13. An implantable device as in claim 10 wherein the paraplegia prevention vent tube is positioned on the tubular body distally of the plurality of low profile side arms.

14. An implantable device as in claim 10 wherein the paraplegia prevention vent tube has a diameter of approximately 6 mm and a length of from 10 to 32 mm.

15. An implantable device as in claim 10 wherein the plurality of low profile side arms comprises four low profile side arms which are so constructed and arranged for connection to the celiac artery, superior mesenteric artery, the right renal artery and the left renal artery; and wherein the paraplegia prevention vent tube is intended for, and is constructed and arranged for, the temporary perfusion of the intercostal arteries.

16. An implantable device comprising
a tubular body of a biocompatible graft material, the tubular body defining a main lumen therethrough; and
a paraplegia prevention vent tube in fluid communication with the main lumen and open to external of the tubular body, the paraplegia prevention vent tube being unstented and open externally in a proximal direction to external of the tubular body, wherein the paraplegia prevention vent tube is not intended to be connected to a side branch vessel but wherein the paraplegia prevention vent tube is intended, and is so constructed and arranged, to provide temporary perfusion to external of the implantable device after deployment of the implantable device into a vessel of the human or animal body and wherein the paraplegia prevention vent tube is intended, and is so constructed and arranged, to be subsequently blocked.

* * * * *